United States Patent
Poncelet et al.

(10) Patent No.: US 12,037,746 B2
(45) Date of Patent: Jul. 16, 2024

(54) METHOD FOR PREPARING A COMPOUND COMPRISING AT LEAST ONE IMINE FUNCTION BY A SPECIFIC CONDENSATION REACTION, AND PARTICULAR APPLICATION OF SAID METHOD IN THE FIELD OF DYEING

(71) Applicant: COMMISSARIAT À L'ÉNERGIE ATOMIQUE ET AUX ÉNERGIES ALTERNATIVES, Paris (FR)

(72) Inventors: Olivier Poncelet, Grenoble (FR); Aurélien Auger, Grenoble (FR)

(73) Assignee: COMMISSARIAT À L'ÉNERGIE ATOMIQUE ET AUX ÉNERGIES ALTERNATIVES, Paris (FR)

( * ) Notice: Subject to any disclaimer, the term of this patent is extended or adjusted under 35 U.S.C. 154(b) by 148 days.

(21) Appl. No.: 17/755,348

(22) PCT Filed: Oct. 20, 2020

(86) PCT No.: PCT/FR2020/051882
§ 371 (c)(1),
(2) Date: Apr. 27, 2022

(87) PCT Pub. No.: WO2021/084185
PCT Pub. Date: May 6, 2021

(65) Prior Publication Data
US 2022/0412011 A1    Dec. 29, 2022

(30) Foreign Application Priority Data
Oct. 29, 2019 (FR) ..................... 1912128

(51) Int. Cl.
| C07C 249/00 | (2006.01) |
| C07C 249/02 | (2006.01) |
| C08B 37/08 | (2006.01) |
| C09B 55/00 | (2006.01) |
| D21H 13/30 | (2006.01) |
| D21H 21/28 | (2006.01) |

(52) U.S. Cl.
CPC .......... D21H 21/28 (2013.01); C07C 249/02 (2013.01); C08B 37/003 (2013.01); C09B 55/009 (2013.01); D21H 13/30 (2013.01)

(58) Field of Classification Search
CPC ........ D21H 21/28; D21H 13/30; D21H 21/24; D21H 21/14; C07C 249/02; C08B 37/003; C09B 55/009; C09B 55/003; C09B 55/004; Y02P 20/54
USPC ............................................. 8/543
See application file for complete search history.

(56) References Cited

U.S. PATENT DOCUMENTS

2014/0018576 A1 * 1/2014 Cantat .................. C07D 231/12
564/132

FOREIGN PATENT DOCUMENTS

| FR | 3015988 A1 | 7/2015 | |
| WO | 2004046087 A1 | 6/2004 | |
| WO | WO 2004046087 A1 * | 6/2004 | .......... C07C 251/24 |
| WO | 2008057312 A2 | 5/2008 | |
| WO | 2015140750 A1 | 9/2015 | |
| WO | 2017158302 A1 | 9/2017 | |

OTHER PUBLICATIONS

International Search Report for PCT/FR2020/051882 dated Dec. 9, 2020 and translation thereof.
Search Report for French application No. 1912128 dated Apr. 20, 2020.

* cited by examiner

*Primary Examiner* — Eisa B Elhilo
(74) *Attorney, Agent, or Firm* — Pearne & Gordon LLP

(57) ABSTRACT

A method for manufacturing a compound comprising at least one imine group, the method comprising a step of reaction between a first compound comprising at least one amine group and a second compound comprising at least one carbonyl group, the reaction step being carried out in the presence of at least one supercritical fluid.

35 Claims, No Drawings

METHOD FOR PREPARING A COMPOUND COMPRISING AT LEAST ONE IMINE FUNCTION BY A SPECIFIC CONDENSATION REACTION, AND PARTICULAR APPLICATION OF SAID METHOD IN THE FIELD OF DYEING

CROSS-REFERENCE TO RELATED APPLICATIONS

This is a National Stage application of PCT international application PCT/FR2020/051882, filed on Oct. 20, 2020, which claims the priority of French Patent Application No. 1912128, filed Oct. 29, 2019, both of which are incorporated herein by reference in their entirety.

TECHNICAL FIELD

The present invention relates to a method for preparing a compound comprising at least one imine function by a specific condensation reaction, this method being able to find application in all fields requiring the transformation of the properties of a base compound by the introduction of a functional group thereon via the formation of at least one imine function, and in particular in that of the dyeing.

This field of application is particularly important faced with the need to be able to have dyed products, such as papers, having a good light-fastness of the dyeing and a good retention of the latter even after exposure to humidity or simple or prolonged contact with different types of solvents, in particular when the dyed product is intended to constitute a packaging product.

Conventionally, the manufacture of dyed papers comprises the following steps:
 the preparation of an aqueous suspension comprising cellulosic fibres and at least one water-soluble dye having a chemical affinity for the fibres and optionally one or more fixing agents, so as to improve the fixing of the dye(s) on the fibres;
 the formation of sheets by depositing the aqueous suspension on a web allowing the draining of suspension.

This manufacturing mode, however, has the drawback of generating aqueous effluents comprising the dye and, consequently, a management of these effluents. In addition, it does not allow avoiding the phenomenon of salting-out the dyes incorporated into the paper, in particular, after a prolonged exposure to a moisture-laden medium, especially as the dyes are not bound to the fibres by strong chemical bonds, the fixing being done rather by simple chemical adsorption and that a portion of the dyes remains simply trapped in the fibrous network.

In order to overcome the drawback linked to the management of the polluted aqueous effluents, dyed papers have been produced, alternatively, by depositing the dye(s), for example, by means of a size press, on the previously formed sheets of paper, the drawback resulting from this technique being the difficulty of uniformly distributing the dye(s) on the surface of the sheets. In addition, the dye(s) are present only on the surface and not in the core of the sheets, which contributes to a dyeing which is unstable and likely to change substantially during the ageing of the sheets.

In order to obtain a deeper and more stable dyeing, the research efforts have focused on the development of innovative techniques for impregnating dyes with paper by emphasising in particular on effective impregnation vectors, such as the use of a supercritical medium to convey the dye(s) to the core of the fibres constituting the paper. Thus, in FR 3 015 988, it is a question of a method for impregnating a paper with an impregnating agent, such as a dye, comprising the following steps:
 a prior step of forming the sheets of paper, which incorporate a specific additive capable of receiving and trapping the impregnating agent, this additive can be a stimulable polymer, such as PEOX or PEG; organic or inorganic particles of the hydrophilic type and including hydrophobic cavities, such as cyclodextrins or modified clays or amphiphilic molecules;
 a step of impregnating the sheets of paper with the impregnating agent by contacting them with said agent by means of a supercritical fluid, such as supercritical $CO_2$.

If this method allows an impregnation to the core of the sheets by the dye and a satisfactory dyeing, the fixing of the dye via the additive is a non-covalent fixing therefore subject to a possibility of salting-out the dye in a wet medium and the papers resulting from this impregnation have unsatisfactory light-fastness.

In WO 2015/140750, the described paper dyeing method also uses a supercritical medium and more specifically, comprises the following steps:
 a step of contacting cellulosic fibres with a compound derived from urea of formula R—NH—CO—$NH_2$ with R representing a linear or branched, saturated or unsaturated hydrocarbon chain, and comprising at least 3 carbon atoms or representing a saturated or unsaturated cyclic hydrocarbon radical bonded directly or via a methylene or ethylene group to the nitrogen atom, whereby a carbamate bond is formed between this compound and the cellulosic fibres;
 a step of contacting the cellulosic fibres thus modified with at least one hydrophobic dye, in a supercritical $CO_2$ medium.

In this method, the bond between the dye and the fibres is performed by a phenomenon of adsorption of the dye at the hydrocarbon units, that is to say the hydrocarbon chains or the cyclic hydrocarbon radicals of the cellulose carbamate. However, this type of bond may prove to be insufficient to guarantee a long-lasting dyeing and prevent the salting-out of the dyes, in particular when the papers thus dyed are subjected to a prolonged contact with a medium which is wet or comprising organic solvent vapours.

Finally, in WO2017/158302, it is also a question of a method for impregnating a paper with a molecule of interest, such as a dye, in a supercritical medium, the impregnation occurring thanks to the addition to the paper to the core and/or at the surface of a polymeric additive introduced in the form of a latex (for example, an aqueous ionic dispersion of polymer particles, whose chains contain Lewis-type base groups, such as ether, carbonyl, carboxyl or phenyl groups), this polymeric additive allowing the trapping of the molecule of interest. However, this method, even if it allows obtaining an effective dyeing, would require improvements to increase the resistance of the dyeing to the leaching of the dyed paper after contacting it with an organic solvent, such as acetone or ethanol or to improve the light-fastness of the dyeing.

In view of what exists and in order to overcome the drawbacks of the methods mentioned above, the authors of the present invention have set themselves the objective, while benefiting from the advantages inherent in the use of a supercritical medium, to develop a specific method for fixing a dye to a cellulosic compound, such as paper, the fixing being established covalently between said dye and said compound via the formation of a specific binding group in a supercritical medium.

Based on this objective, the authors of the present invention have discovered, surprisingly, that it is possible, in a supercritical medium, to react two compounds including respectively a carbonyl group and an amine group to form therebetween an imine binding group, thus opening the field of the invention to all fields requiring the transformation of the properties of a base compound by the introduction of a functional group thereon via the formation of at least one imine binding group.

DISCLOSURE OF THE INVENTION

Thus, the invention relates to a method for manufacturing a compound comprising at least one imine group, said method comprising a step of reaction between a first compound comprising at least one amine group and a second compound comprising at least one carbonyl group, said reaction step being carried out in the presence of at least one supercritical fluid.

Thanks to the use of at least one supercritical fluid to implement this reaction, a much faster reaction rate was observed relative to a similar reaction carried out in a medium comprising an organic solvent under non-supercritical conditions (for example, from 30 minutes to 3 hours with the supercritical fluid against several days, or even 1 week with the conventional solvent medium).

The term "supercritical fluid", means a fluid brought to a pressure and a temperature beyond its critical point, corresponding to the temperature and pressure pair (respectively Tc and Pc), for which the liquid phase and the gaseous phase has the same density and beyond which the fluid is in its supercritical range. Under supercritical conditions, the fluid has a very increased dissolving power relative to the same fluid under non-supercritical conditions and thereby facilitates the solubilisation of the first compound and/or of the second compound, thus facilitating the reactivity therebetween.

Preferably, the reaction step is carried out in the presence of a single supercritical fluid, which is preferably supercritical $CO_2$, in particular due to its low critical temperature (31° C.), which allows implementing the low-temperature reaction without risk of degradation of the first compound and/or of the second compound. More specifically, supercritical $CO_2$ is obtained by heating carbon dioxide beyond its critical temperature (31° C.) and compressing it above its critical pressure (73 bars). In addition, supercritical $CO_2$ is non-flammable, non-toxic, relatively inexpensive and does not require reprocessing after the method, compared to methods involving the use of organic solvents.

As mentioned above, the method of the invention comprises a reaction step between a first compound comprising at least one amine group and a second compound comprising at least one carbonyl group, said reaction step being carried out in the presence of at least a supercritical fluid (provided that the amine group(s) of the first compound and the carbonyl group(s) of the second compound react together to form the imine group(s), the compound resulting from the reaction step thus resulting from a reaction of condensation between the first compound and the second compound).

Concerning the first compound, the amine group(s) are preferably primary amine groups (that is to say groups of formula $-NH_2$) and concerning the second compound, the carbonyl group(s) are preferably aldehyde groups, a primary amine group and an aldehyde group being capable of effectively reacting by a condensation reaction to form an imine group.

The term "imine group" means a group having the following formula:

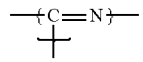

the two braces placed at the carbon atom indicating that said carbon atom is bonded to two other atoms to ensure its tetravalency, these two other atoms belonging to a remainder of the second compound and the brace placed at the nitrogen atom indicating that said nitrogen atom is bonded to another atom to ensure its trivalency, the other atom belonging to a radical of the first compound.

Concerning the first compound and the second compound, it is advantageously understood that at least one of said compounds is capable of being solubilised in the supercritical fluid used in the context of the method of the invention.

According to one first embodiment, the reaction step can be implemented in a reactor, for example an autoclave, by the following sequence of operations:
  an operation of contacting the first compound, the second compound and the fluid under non-supercritical conditions;
  an operation of bringing the mixture comprising the fluid, the first compound and the second compound under supercritical conditions, the supercritical conditions once established being maintained until completion of the reaction step.

According to one second embodiment, the reaction step can be implemented in a reactor, for example an autoclave, by the following sequence of operations:
  an operation of introducing a fluid into the reactor under non-supercritical conditions;
  an operation of bringing the fluid under supercritical conditions;
  an operation of introducing the first compound and the second compound into the reactor, the supercritical conditions being maintained until completion of the reaction step.

The method of the invention may consist, in particular, in a method for changing the properties of a base compound (the first compound or the second compound) by the introduction of a functional group (belonging to the first compound when the base compound is the second compound or belonging to the second compound when the base compound is the first compound) thereon via the formation of at least one imine binding group by reaction between the amine group(s) of the first compound and the carbonyl group(s) of the second compound, the change in the properties may consist in a dyeing.

More specifically, the method of the invention is quite suitable for being a dyeing method, in which case one of the compounds, namely the first compound or the second compound, is a dye compound (more specifically, a compound comprising at least one chromophore group) and the other compound (namely, the first compound if the second compound is a dye compound or the second compound if the first compound is a dye compound) is a compound intended to be dyed. The obtained dyeing is more stable than that obtained with the methods of the prior art, due to the fact that, at the end of the method, the dye compound is covalently bonded (via an imine group) to the compound intended to be dyed.

More specifically, the first compound is a compound intended to be dyed and the second compound is a dye compound, said method of the invention thus being a dyeing method.

The first compound can be any compound including at least one amine group and, in particular, when the method consists of a dyeing method, the first compound can be a polymer comprising, at all or part of the repeating units thereof, at least one amine group. More specifically, it may be a polymer belonging to the chitosan family, that is to say polyosides resulting from the random distribution of β(1-4)-linked D-glucosamine units and N-acetyl-D-glucosamine units. Chitosans are biodegradable biopolymers.

In this case, the first compound can be, in particular, integrated into a sheet of paper (up to, for example, 20% by weight), the method thus consisting, when the second compound is a dye compound, in a method for obtaining dyed paper by dyeing sheet(s) based on chitosan.

The second compound can be any compound comprising at least one carbonyl group, preferably an aldehyde group and, in particular, when the method consists of a dyeing method, the second compound is, advantageously, a dye compound (or in other words, a compound comprising at least one chromophore group), which means that the second compound, by reacting via a carbonyl group with an amine group of the first compound to form an imine group, will give a colour to the first compound.

More specifically, the second compound may be a compound comprising one or more aromatic rings, the or all or part of said aromatic rings comprising:
  at least one carbonyl group; and
  optionally at least one other group different from a carbonyl group and comprising at least one atom bearing a lone pair, which covers the following situations:
  the compound comprises a single aromatic ring, for example an aromatic carbon ring (that is to say in which all constituent atoms of the ring are carbon atoms) or comprising at least one heteroatom (the aromatic ring can thus be referred to as heteroaromatic ring), said aromatic ring comprising at least one carbonyl group and optionally at least one other group different from a carbonyl group and comprising at least one atom bearing a lone pair;
  the compound comprises several aromatic rings, all or part of said rings being aromatic carbon rings (that is to say in which all constituent atoms of the ring(s) are carbon atoms) or comprising at least one heteroatom and comprising at least one carbonyl group and all or part of said cycles optionally comprising at least one other group different from a carbonyl group and comprising at least one atom bearing a lone pair.

According to one first embodiment, the second compound is an aromatic compound comprising a single aromatic ring, which aromatic ring is bearing at least one carbonyl group and at least one other group different from a carbonyl group and comprising at least one atom bearing a lone pair.

Concerning the other group different from a carbonyl group and comprising at least one atom bearing a lone pair, it may be a group comprising an oxygen atom, a sulphur atom and/or a nitrogen atom, preferably an electron withdrawing group and with a donor mesomeric effect, such as a group comprising an oxygen atom, for example a hydroxyl group.

In particular, the second compound may consist of a monocyclic aromatic carbon compound (which means that all constituent atoms of the ring are carbon atoms), for example, six-membered (such as a phenyl group), it being understood, in this case, that this ring bears both at least one carbonyl group and at least one other group different from a carbonyl group and comprising at least one atom bearing a lone pair, (for example, an oxygen atom, a sulphur atom and/or a nitrogen atom), such as an electron withdrawing group and with a donor mesomeric effect, for example comprising an oxygen atom, such as a hydroxyl group.

More specifically, the second compound may consist of a monocyclic aromatic carbon compound (that is to say in which all constituent atoms of the ring are carbon atoms), such as a phenyl group, bearing a single carbonyl group and a single other group different from a carbonyl group and comprising at least one atom bearing a lone pair (for example, an oxygen atom, a sulphur atom and/or a nitrogen atom), such an electron withdrawing group and with a donor mesomeric effect, for example comprising an oxygen atom, such as a hydroxyl group, said carbonyl group and the other group being in the ortho position to each other on the aromatic carbon ring. This type of compound is capable of dissipating the energy absorbed by rotation and allows, after reaction with a first compound to form an imine group, to give a colour to the first compound having good light-fastness.

Furthermore, the aromatic ring may comprise one or more other groups than those mentioned above, for example groups chosen from halogen atoms, alkyl groups, alkoxy groups, ester groups.

By way of example of a second compound, mention may be made of a compound having the following formula (I):

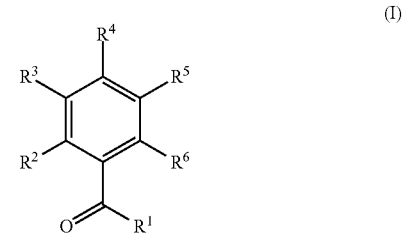

wherein:
R$^1$ represents a hydrogen atom or an alkyl group, preferably a hydrogen atom;
R$^2$ represents a group different from a carbonyl group and comprising an electron withdrawing oxygen atom and with a donor mesomeric effect, such as a hydroxyl group;
R$^3$ to R$^6$ represent, independently of each other, a hydrogen atom, an alkyl group, an alkoxy group, an ester group.

More specifically, at least one of the groups R$^3$ to R$^6$ is an ester group and, even more specifically, only one of the groups R$^3$ to R$^6$ is an ester group, the other groups being a hydrogen atom.

A compound meeting these specificities is a group of the following formula (II):

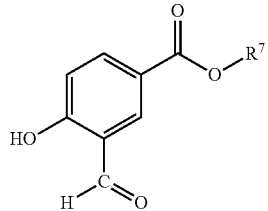

(II)

wherein $R^7$ represents an alkyl group, such as an ethyl group.

When this compound of formula (II) is reacted with a first compound of the chitosan family, which is integrated into a sheet of paper (for example, up to 20% by weight), the sheet of paper displays, after reaction, an intense yellow colour and showing strong fluorescence under UV illumination (365 nm).

According to one second embodiment, the second compound is an aromatic compound comprising several aromatic rings, for example, two aromatic rings, said aromatic rings being fused, at least one of said rings comprising at least one carbonyl group and at least one of said rings comprising at least one other group different from a carbonyl group and comprising at least one atom bearing a lone pair.

Concerning the other group, it may be a group comprising an oxygen atom, a sulphur atom and/or a nitrogen atom, preferably an electron withdrawing group and with a donor mesomeric effect, such as a group comprising an oxygen atom, for example, a hydroxyl group.

In particular, the second compound may consist of a bicyclic aromatic compound, whose rings are fused, one of the rings being a heteroaromatic ring, while the other ring is an aromatic carbon ring (that is to say in which all constituent atoms of the ring are carbon atoms), for example, 6-membered (such as a phenyl group), one of the rings is bearing at least one carbonyl group and one of the rings is bearing at least one other group different from a carbonyl group and comprising at least one atom bearing a lone pair (for example, an oxygen atom, a sulphur atom and/or a nitrogen atom), such as an electron withdrawing group and with a donor mesomeric effect, for example comprising an oxygen atom, such as a hydroxyl group.

More specifically, the second compound may consist of a bicyclic aromatic compound, whose rings are fused, one of the rings being a heteroaromatic ring, while the other ring is an aromatic carbon ring, (which means that all constituent atoms of the ring are carbon atoms), for example, 6-membered (such as a phenyl group), the heteroaromatic ring is bearing at least one carbonyl group and the aromatic carbon ring is bearing at least one other group different from a carbonyl group and comprising at least one atom bearing a lone pair (for example, an oxygen atom, a sulphur atom and/or a nitrogen atom), such as an electron withdrawing group and with a donor mesomeric effect, such as a hydroxyl group.

By way of example of a second compound, mention may be made of a group having the following formula (III):

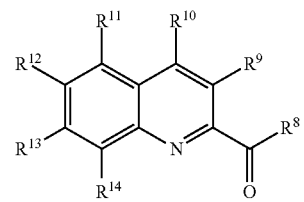

(III)

wherein:

$R^8$ represents a hydrogen atom or an alkyl group, preferably, a hydrogen atom;

$R^{14}$ represents a group different from a carbonyl group and comprising an electron withdrawing oxygen atom and with a donor mesomeric effect;

$R^9$ to $R^{19}$ represent, independently of each other, a hydrogen atom, an alkyl group, an alkoxy group, an ester group.

A specific compound meeting these specificities is a group of the following formula (IV):

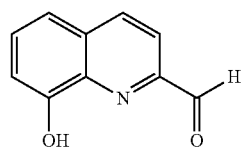

(IV)

this compound corresponding to 8-hydroxy-2-quinolinecarboxaldehyde.

Moreover, at least one of the first or second compound has a melting temperature less than the operating temperature of the reaction step and, more specifically, at least one of the first or second compounds has a melting temperature less than 120° C., or even less than or equal to 100° C. Under such conditions, at least one of the first or second compounds is in the liquid state under the operating conditions of the reaction step (these operating conditions being conditions necessary for the fluid to be under supercritical conditions), which allows a better transport and a better activation of the compounds to generate the condensation reaction.

More specifically, the second compound has a melting temperature less than the operating temperature of the reaction in the presence of at least one supercritical fluid and, more specifically, the melting temperature of the second compound may be less than 120° C., or even less than or equal to 100° C., which allows it to be in the liquid state under the operating conditions of the reaction step, which allows a better vectorisation thereof towards the first compound and therefore facilitating the condensation reaction between the first compound and the second compound.

Among the compounds obtained according to the method of the invention, some are new and, in particular, the compounds likely of being obtained by the method of the invention and being compounds of the chitosan family functionalised by groups, called groups A, comprising one or more aromatic rings, the or all or part of said aromatic rings comprising at least one imine group and the or all or part of said rings comprising at least one other group different from an imine group and comprising at least one atom bearing a lone pair.

It is specified, the term "functionalised" means, within the meaning of the invention, an attachment of the aforementioned groups to the compounds by means of covalent bonds.

As mentioned above, these compounds belong to the chitosan family, that is to say polyosides resulting from the random distribution of ß(1-4))-linked D-glucosamine units and N-acetyl-D-glucosamine, all or part of the D-glucosamine units having their amine groups transformed into imine groups, said imine groups being those belonging to the groups A, which means in other words, that the groups A are bonded to the chitosan polymers at the positions originally occupied by the amine groups thereof, which are converted into imine groups. In this particular case, the concerned polymer constitutes a chitosan radical, due to the fact that the amine groups are wholly or partly converted into imine groups, which imine groups now form part of the groups A.

According to one first embodiment, the groups A consist of aromatic groups comprising a single aromatic ring, which aromatic ring is bearing at least one imine group and at least one other group different from an imine group and comprising at least one atom bearing a lone pair.

Concerning the other group, it may be a group comprising an oxygen atom, a sulphur atom and/or a nitrogen atom, preferably an electron withdrawing group and with a donor mesomeric effect, such as a substituent comprising an oxygen atom, for example, a hydroxyl substituent.

In particular, the groups A can consist of monocyclic aromatic carbon groups (which means that all constituent atoms of the rings are carbon atoms), for example, 6-membered (such as a phenyl group), it being understood, in this case, that the ring of the groups is bearing both at least one imine group and at least one other group different from an imine group and comprising at least one atom bearing a lone pair (for example, an oxygen atom, a sulphur atom and/or a nitrogen atom), such as an electron withdrawing group and with a donor mesomeric effect, for example comprising an oxygen atom, such as an hydroxyl group.

More specifically, the groups A can consist of monocyclic aromatic carbon groups, for example, a phenyl group, bearing a single imine group and a single other group different from an imine group and comprising at least one atom bearing a lone pair (for example, an oxygen atom, a sulphur atom and/or a nitrogen atom), such as an electron withdrawing group and with a donor mesomeric effect, for example comprising an oxygen atom, such as a hydroxyl group, said imine group and the other group being in the ortho position to each other on the aromatic ring.

Furthermore, the constituent aromatic ring of these groups may comprise one or more other groups, such as those mentioned above, for example, groups selected from halogen atoms, alkyl groups, alkoxy groups, ester groups.

By way of example of groups A, mention may be made of groups having the following formula (V):

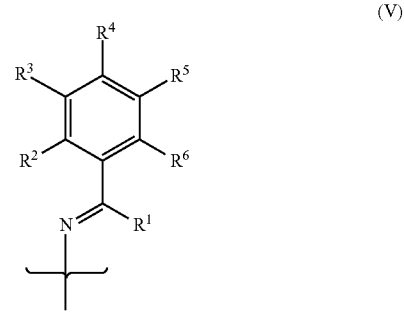

wherein:
$R^1$ represents a hydrogen atom or an alkyl group; preferably a hydrogen atom;
$R^2$ represents a group comprising an electron withdrawing oxygen atom and with a donor mesomeric effect; such as an hydroxyl group;
$R^3$ to $R^6$ represent, independently of each other, a hydrogen atom, an alkyl group, an alkoxy group, an ester group,
the brace indicating where the group A is bound to the chitosan radical either directly (which means that the nitrogen atom is directly covalently bonded to the chitosan radical) or via an organic spacer group (which means that the organic spacer group forms a bridge between the nitrogen atom and the chitosan radical), this organic spacer group may be an alkylene group.

More specifically, at least one of the groups $R^3$ to $R^6$ is an ester group and, even more specifically, only one of the groups $R^3$ to $R^6$ is an ester group, the other groups being a hydrogen atom.

A group A meeting these specificities is a group of the following formula (VI):

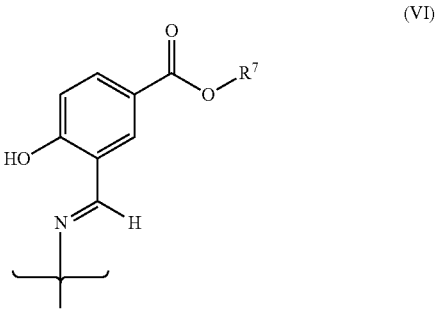

wherein $R^7$ represents an alkyl group and the brace indicating where the group A is bound to the chitosan radical either directly (which means that the nitrogen atom is directly covalently bonded to the chitosan radical) or via an organic spacer group (which means that the organic spacer group forms a bridge between the nitrogen atom and the chitosan radical).

According to one second embodiment, the groups A can consist of aromatic groups comprising several aromatic rings, for example two aromatic rings, said aromatic rings being fused, at least one of said rings comprising at least one imine group and at least one of said rings comprising at least one other group different from an imine group and comprising at least one atom bearing a lone pair.

Concerning the other group, it may be a group comprising an oxygen atom, a sulphur atom and/or a nitrogen atom, preferably an electron withdrawing group and with a donor mesomeric effect, such as a group comprising an oxygen atom, for example, a hydroxyl group.

In particular, the groups A can consist of bicyclic aromatic groups, whose rings are fused, one of the rings being a heteroaromatic ring, while the other ring is an aromatic carbon ring (that is to say in which all constituent atoms of the ring are carbon atoms), for example, 6-membered (such as a phenyl group), it being understood that one of the rings is bearing at least one imine group and one of the rings is bearing at least one other group different from an imine group and comprising at least one atom bearing a lone pair (for example, an oxygen atom, a sulphur atom and/or an nitrogen atom), such as an electron withdrawing group and with a donor mesomeric effect, for example comprising an oxygen atom, such as a hydroxyl group.

More specifically, the groups A may consist of bicyclic aromatic groups, whose rings are fused, one of the rings being a heteroaromatic ring, while the other ring is an aromatic carbon ring (which means that all constituent atoms of the ring are carbon atoms), for example, 6-membered (such as a phenyl group), the heteroaromatic ring is bearing at least one imine group and the aromatic carbon ring is bearing at least one other group different from an imine group and comprising at least one atom bearing a lone pair (for example, an oxygen atom, a sulphur atom and/or a nitrogen atom), such as an electron withdrawing group and with a donor mesomeric effect, for example comprising an oxygen atom, such as a hydroxyl group.

By way of example of groups A, mention may be made of a group having the following formula (VII):

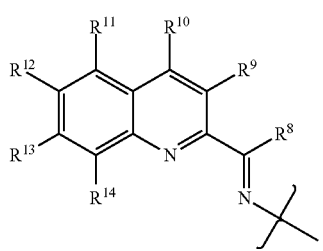

(VII)

wherein:

R$^8$ represents a hydrogen atom or an alkyl group; preferably a hydrogen atom;

R$^{14}$ represents a group comprising an electron withdrawing oxygen atom and with a donor mesomeric effect, such as a hydroxyl group;

R$^9$ to R$^{13}$ represent, independently of each other, a hydrogen atom, an alkyl group, an alkoxy group, an ester group, the brace indicating where the group A is bound to the chitosan radical either directly (which means that the nitrogen atom is directly covalently bonded to the chitosan radical) or via an organic spacer group (which means that the organic spacer group forms a bridge between the nitrogen atom and the chitosan radical).

A specific group A corresponding to these specificities is a group of the following formula (VIII):

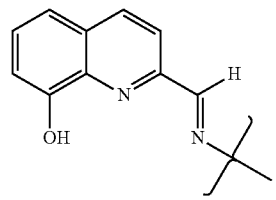

(VIII)

The compounds belonging to the chitosan family in accordance with the invention can be advantageously incorporated into paper to give it a colour which is stable over time and which is not likely to undergo a leaching after being contacted with moisture or an organic solvent.

Thus, the invention also relates to a paper comprising at least one compound belonging to the chitosan family in accordance with the invention, this compound may be present up to at least 20% by weight relative to the total weight of the paper.

Other features and advantages of the invention will appear from the additional following description which relates to two examples of preparation. Of course, this additional description is only given by way of illustration of the invention and in no way constitutes a limitation thereof.

DETAILED DISCLOSURE OF PARTICULAR EMBODIMENTS

Example 1

This example illustrates a method in accordance with the invention and, more specifically, a method for dyeing a paper.

The concerned paper is a specific paper comprising a chitosan up to 20% by weight, which is a natural polymer having pendant primary amine groups, which groups are very reactive to react with aldehyde groups and form imine groups.

The aforementioned paper is placed in a reactor filled with supercritical $CO_2$ and a compound of formula (II) in which R$^7$ is an ethyl group.

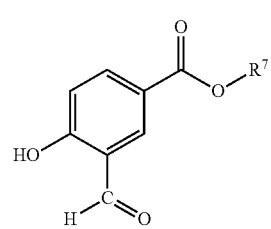

(II)

this compound corresponding to ethyl 3-formyl-4-hydroxybenzoate.

The pressure is set at 280 bars and the temperature is set at 105° C., whereby the $CO_2$ is in the supercritical state. Under these conditions, ethyl 3-formyl-4-hydroxybenzoate is in liquid form knowing that its melting point is 67-73° C. and is soluble in supercritical $CO_2$ given its lipophilic nature due to the presence of an ethyl benzoate group. The aforementioned pressure and temperature are maintained for 1 hour.

At the end of this period, the resulting paper displays an intense yellow colour.

In order to confirm the efficiency of the method, in parallel, the same reaction was carried out with an identical paper sample and the same aldehyde but in ethanol. It took 2 weeks using a wet process to bring this dyeing reaction to completion, thus highlighting the considerable time saving to reproduce this reaction under supercritical $CO_2$.

Standardized (ISO 105-B02) light-fastness and colour fastness tests have been conducted in order to assess the colorimetric performance of the dyed sample obtained under supercritical $CO_2$. Thus the light-fastness under UV of the sample was assessed at 3. For paper manufacturers, the cellulosic substrates are considered as having a suitable light-fastness from 3. The colour fastness, for its part, was assessed at 3-4, which is satisfactory.

Finally, in order to confirm the covalent attachment of the dye to the paper, the dyed sample was subjected to cleaning then to leaching with acetone and ethanol. After drying at ambient temperature, the sample retains a good yellow tint. The confirmation of the covalent attachment of the dye via the formation of an imine function (C=N) was validated by IR spectroscopy, with observation of the stretching band of the C=N function at 1635 cm$^{-1}$, a band which is absent on the original paper.

Example 2

This example illustrates a method in accordance with the invention and a compound obtained in accordance with the method of the invention and in accordance with the invention, this compound resulting from the condensation of a chitosan polymer with a compound of the following formula (IV):

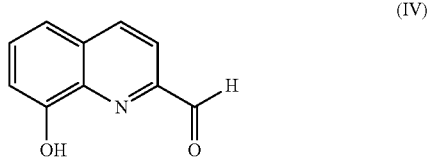 [SMILES: O=Cc1ccc2cccc(O)c2n1]

(IV)

These two reagents are placed in a reactor filled with $CO_2$, the pressure being set at 260 bars and the temperature is set at 105° C., whereby the $CO_2$ is in the supercritical state. Under these conditions, 8-hydroxy-2-quinolinecarboxaldehyde is in liquid form knowing that its melting point is 87-100° C. The aforementioned pressure and temperature are maintained for 3 hours At the end of this period, the initially colourless chitosan displays an orange tint, typical of the increase in the conjugated system and proof that the chitosan and 8-hydroxy-2-quinolinecarboxaldehyde have reacted together covalently.

What is claimed is:

1. A method for manufacturing a compound comprising at least one imine group, said method comprising a step of reaction between a first compound comprising at least one amine group and a second compound comprising at least one carbonyl group, said reaction step being carried out in the presence of at least one supercritical fluid.

2. The method according to claim 1, wherein the reaction step is carried out in the presence of a single supercritical fluid, which is supercritical $CO_2$.

3. The method according to claim 1, wherein, for the first compound, the amine group(s) are primary amine groups and, for the second compound, the carbonyl group(s) are aldehyde groups.

4. The method according to claim 1, wherein, for the first compound and the second compound, at least one of said compounds is capable of being solubilised in the supercritical fluid.

5. The method according to claim 1, wherein the reaction step is implemented in a reactor by the following sequence of operations:
an operation of contacting the first compound, the second compound and the fluid under non-supercritical conditions;
an operation of bringing the mixture comprising the fluid, the first compound and the second compound under supercritical conditions, the supercritical conditions once established being maintained until completion of the reaction step.

6. The method according to claim 1, wherein the reaction step is implemented in a reactor by the following sequence of operations:
an operation of introducing a fluid into the reactor under non-supercritical conditions;
an operation of bringing the fluid under supercritical conditions;
an operation of introducing the first compound and the second compound into the reactor, the supercritical conditions being maintained until completion of the reaction step.

7. The method according to claim 1, wherein one of the compounds, namely the first compound or the second compound, is a dye compound and the other compound is a compound intended to be dyed, said method thus being a dyeing method.

8. The method according to claim 1, wherein the first compound is a compound intended to be dyed and the second compound is a dye compound, said method thus being a dyeing method.

9. The method according to claim 1, wherein the first compound is a polymer comprising, at all or part of the repeating units thereof, at least one amine group.

10. The method according to claim 1, wherein the first compound is a polymer belonging to the chitosan family.

11. The method according to claim 10, wherein the first compound is integrated into a sheet of paper.

12. The method according to claim 1, wherein the second compound is a compound comprising one or more aromatic rings, wherein at least one of the one or more aromatic rings comprises at least one carbonyl group and optionally at least one other group different from a carbonyl group. and wherein at least one of the one or more aromatic rings comprises at least one atom bearing a lone pair.

13. The method according to claim 1, wherein the second compound is an aromatic compound comprising a single aromatic ring, which aromatic ring is bearing at least one carbonyl group and at least one other group different from a carbonyl group and comprising at least one atom bearing a lone pair.

14. The method according to claim 1, wherein the second compound is a monocyclic aromatic carbon compound.

15. The method according to claim 1, wherein the second compound is a monocyclic aromatic carbon compound bearing a single carbonyl group and a single other group different from a carbonyl group and comprising at least one atom bearing a lone pair, said carbonyl group and the other group being in the ortho position to each other on the aromatic carbon ring.

16. The method according to claim 1, wherein the second compound is a compound having the following formula (I):

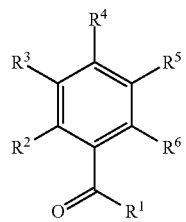

(I)

wherein:

R¹ represents a hydrogen atom or an alkyl group;

R² represents a group different from a carbonyl group and comprising an electron withdrawing oxygen atom and with a donor mesomeric effect, R³ to R⁶ represent, independently of each other, a hydrogen atom, an alkyl group, an alkoxy group, an ester group.

17. The method according to claim 1, wherein the second compound is a compound of the following formula (II):

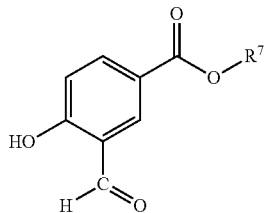

(II)

wherein R⁷ represents an alkyl group.

18. The method according to claim 1, wherein the second compound is an aromatic compound comprising several aromatic rings, said aromatic rings being fused, at least one of said aromatic rings comprising at least one carbonyl group and at least one of said aromatic rings comprising at least one other group different from a carbonyl group and comprising at least one atom bearing a lone pair.

19. The method according to claim 1, wherein the second compound is a bicyclic aromatic compound, whose aromatic rings are fused, one of the aromatic rings being a heteroaromatic ring, while the other ring is an aromatic carbon ring, one of the aromatic rings is bearing at least one carbonyl group and one of the aromatic rings is bearing at least one other group different from a carbonyl group and comprising at least one atom bearing a lone pair.

20. The method according to claim 1, wherein the second compound is a bicyclic aromatic compound, whose aromatic rings are fused, one of the aromatic rings being a heteroaromatic ring, while the other aromatic ring is an aromatic carbon ring, the heteroaromatic ring is bearing at least one carbonyl group and the aromatic carbon ring is bearing at least one other group different from a carbonyl group and comprising at least one atom bearing a lone pair.

21. The method according to claim 1, wherein the second compound has the following formula (III):

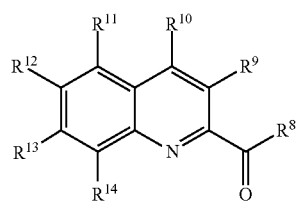

(III)

wherein:

R⁸ represents a hydrogen atom or an alkyl group;

R¹⁴ represents a group different from a carbonyl group and comprising an electron withdrawing oxygen atom and with a donor mesomeric effect;

R⁹ to R¹³ represent, independently of each other, a hydrogen atom, an alkyl group, an alkoxy group, an ester group.

22. The method according to claim 1, wherein the second compound has the following formula (IV):

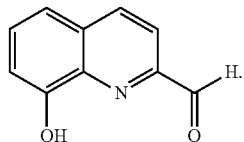

(IV)

23. The method according to claim 1, wherein at least one of the first or second compounds has a melting temperature less than the operating temperature of the reaction step.

24. The method according to claim 1, wherein at least one of the first or second compounds has a melting temperature less than 120° C.

25. A compound capable of being obtained by the method as defined in claim 1, which is a compound of the chitosan family functionalised by groups, called groups A, comprising one or more aromatic rings, wherein at least one of the one or more aromatic rings comprises at least one imine group and wherein at least one of the one or more aromatic rings comprises at least one other group different from an imine group and wherein at least one of the one or more aromatic rings comprises comprising at least one atom bearing a lone pair.

26. The compound according to claim 25, wherein the groups A consist of aromatic groups comprising a single aromatic ring, which aromatic ring is bearing at least one imine group and at least one other group different from an imine group and comprising at least one atom bearing a lone pair.

27. The compound according to claim 25, wherein the groups A consist of monocyclic aromatic carbon groups, the aromatic ring of the groups is bearing both at least one imine group and at least one other group different from an imine group and comprising at least one atom bearing a lone pair.

28. The compound according to claim 25, wherein the groups A consist of monocyclic aromatic carbon groups bearing a single imine group and a single other group different from an imine group and comprising at least one atom bearing a lone pair, said imine group and the other group being in the ortho position to each other on the aromatic ring.

29. The compound according to claim 25, wherein the groups A have the following formula (V):

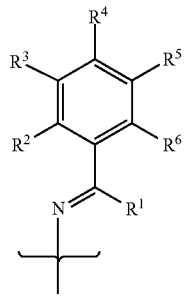

(V)

wherein:
R¹ represents a hydrogen atom or an alkyl group;
R² represents a group comprising an electron withdrawing oxygen atom and with a donor mesomeric effect;
R³ to R⁶ represent, independently of each other, a hydrogen atom, an alkyl group, an alkoxy group, an ester group,
the brace indicating where the group A is bound to the chitosan radical either directly or via an organic spacer group.

30. The compound according to claim 25, wherein the groups A have the following formula (VI):

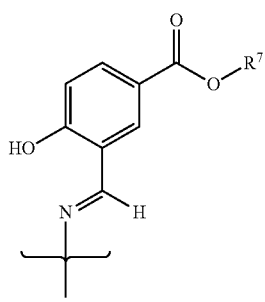

(VI)

wherein R⁷ represents an alkyl group and the brace indicating where the group A is bound to the chitosan radical either directly or via an organic spacer group.

31. The compound according to claim 25, wherein the groups A consist of aromatic groups comprising several aromatic rings, said aromatic rings being fused, at least one of said aromatic rings comprising at least one imine group and at least one of said aromatic rings comprising at least one other group different from an imine group and comprising at least one atom bearing a lone pair.

32. The compound according to claim 25, wherein the groups A consist of bicyclic aromatic groups, whose aromatic rings are fused, one of the aromatic rings being a heteroaromatic ring, while the other ring is an aromatic carbon ring, one of the aromatic rings is bearing at least one imine group and one of the aromatic rings is bearing at least one other group different from an imine group and comprising at least one atom bearing a lone pair.

33. The compound according to claim 25, wherein the groups A consist of bicyclic aromatic groups, whose aromatic rings are fused, one of the aromatic rings being a heteroaromatic ring, while the other ring is an aromatic carbon ring, the heteroaromatic ring is bearing at least one imine group and the aromatic carbon ring is bearing at least one other group different from an imine group and comprising at least one atom bearing a lone pair.

34. The compound according to claim 25, wherein the groups A has the following formula (VII):

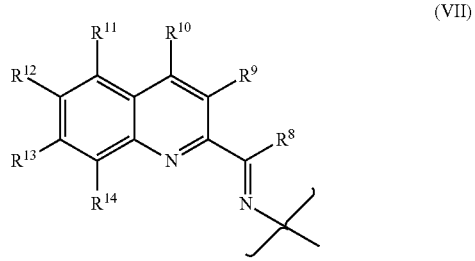

(VII)

wherein:
R⁸ represents a hydrogen atom or an alkyl group;
R¹⁴ represents a group comprising an electron withdrawing oxygen atom and with a donor mesomeric effect;
R⁹ to R¹³ represent, independently of each other, a hydrogen atom, an alkyl group, an alkoxy group, an ester group,
the brace indicating where the group A is bound to the chitosan radical either directly or via an organic spacer group.

35. A paper comprising at least one compound belonging to the chitosan family as defined according to claim 25.

* * * * *